United States Patent [19]

Hauxwell et al.

[11] 3,963,432

[45] June 15, 1976

[54] AQUEOUS COMPOSITIONS FOR USE IN APPLYING DYESTUFFS

[75] Inventors: Frank Hauxwell; Henry Roy Murton, both of Manchester, England

[73] Assignee: Imperial Chemical Industries Limited, London, England

[22] Filed: Mar. 13, 1974

[21] Appl. No.: 450,864

Related U.S. Application Data

[62] Division of Ser. No. 407,952, Oct. 19, 1973, abandoned.

[30] Foreign Application Priority Data

Oct. 27, 1972 United Kingdom............. 49584/72

[52] U.S. Cl........................................ 8/93; 8/173; 252/182
[51] Int. Cl.$^2$.................. C09B 67/00; D06P 1/58; D06P 1/62
[58] Field of Search ................ 8/93, 173; 252/182

[56] References Cited
UNITED STATES PATENTS

| | | |
|---|---|---|
| 2,069,215 | 2/1937 | Chambers ............................ 8/93 |
| 3,056,644 | 10/1962 | Radley et al. ........................ 8/93 |
| 3,440,001 | 4/1969 | Szilagyi ............................... 8/93 |
| 3,442,600 | 5/1969 | Daeuble et al. ..................... 8/93 |
| 3,467,485 | 9/1969 | Schaeuble et al. .................. 8/93 |
| 3,706,525 | 12/1972 | Blackwell et al. ................... 8/173 |

OTHER PUBLICATIONS

Diserens–Dyeing & Printing, Reinhold, N.Y. (1948), pp. 7-22.

*Primary Examiner*—H.S. Cockeram
*Attorney, Agent, or Firm*—Cushman, Darby & Cushman

[57] ABSTRACT

Aqueous compositions, which are aqueous solutions or suspensions of effect materials containing anionic or cationic surface active agents and condensates of from one to four molar proportions of ethylene oxide with aliphatic alcohols having from seven to fifteen carbon atoms, have good wetting properties and are valuable for applying the effect materials to solid substrates. Suitable effect materials include dyestuffs, textile finishing agents, biocides and especially agrochemicals such as herbicides, fungicides and pesticides.

10 Claims, No Drawings

AQUEOUS COMPOSITIONS FOR USE IN APPLYING DYESTUFFS

This is a division, of application Ser. No. 407,952 filed Oct. 19, 1973 now abandoned.

This invention relates to aqueous surface-active agent compositions having improved wetting properties.

According to the invention there are provided aqueous surface active agent compositions having improved wetting properties for use in applying effect materials to solid surfaces which contain one or more cationic or one or more anionic surface active agents and one or more condensates of from one to four molar proportions of ethylene oxide with an aliphatic alcohol containing from seven to fifteen carbon atoms and an effect material.

By wetting is meant the ability of the aqueous composition to displace another fluid, which may be a liquid but will usually be a gas, especially air, from juxtaposition with a solid or from the interstices of a porous solid. Substantially complete wetting is of importance in a nunber of industrial and agricultural applications.

For example in the wet dyeing or finishing of textile materials air must be completely displaced from the interstices of the textile by the dyeing or finishing bath liquors. Many textile materials, notably those made from synthetic polymers, are hydrophobic and approach the behaviour of paraffin wax in their reluctance to be wet by water and it is frequently necessary to improve the wetting properties of the bath liquors in order to obtain satisfactory dyeing or finishing.

Similarly during the drying stage following a dyeing operation there is often a tendency for the dyebath liquor still adhering to the textile material to migrate to that side of the textile material from which evaporation of the water is predominantly taking place. This migration carries with it a certain amount of dyestuff and creates a two-sided effect in the finished article. Improvement in the wetting properties of the dyebath liquor minimises this effect. Other inhomogeneous dyeing effects, such as frostiness, are also minimised.

As an example from a different area of technology, glazes applied to ceramics decorated with resin-containing transfers frequently give an uneven finish due to incomplete wetting of the hydrophobic transfer surface. Smooth finishes may be obtained by improving the wetting properties of the glaze slurry used.

In agriculture, materials used as for example pesticides or fungicides are applied to the foliage of plants by spraying in the form of aqueous dispersions or solutions or to seeds by tumbling. The effectiveness of these materials is generally dependent upon the extent to which they spread over the surface of the foliage or seeds and therefore upon the wetting properties of the dispersion or solution.

Furthermore, the performance of a number of effect materials, such as dyestuffs and agricultural chemicals, depends on obtaining a fine dispersion of them in water before use. Total displacement by water of air from powders of such materials is an essential prerequisite for good dispersion and is aided by the combination of anionic or cationic agent and ethylene oxide condensate. By effect material is meant any material or combination of materials which is to be applied to the surface of a solid substrate in order to affect the properties of the substrate or its surface.

As effect materials there are mentioned for example textile lubricants, spin finishes, antistatic agents, softening agents, optical brightening agents, paper treating agents, electroconductive agents for reprographic papers, detergents and additives, anti soil redeposition systems, metal treating compounds, pickling agents, restraining agents, anti corrosives, film-forming polymers as in emulsion paints, polishing materials, pottery glazes, biocides and especially agrochemicals, in particular herbicides, fungicides or pesticides.

The extent to which wetting has occurred after application of an aqueous composition to a solid can be assessed in a variety of ways, the appropriateness of which vary from case to case.

The simplest assessment in the case of a solid surface is by observing the extent to which spreading has taken place. A quantative measure of the ability to spread can be obtained in terms of the 'contact angle' when spreading is incomplete. The contact angle is the angle contained between the plane of contact of the solid surface with the aqueous composition and a tangent to the droplet of aqueous composition at the point where it meets both the solid surface and the air. A low contact angle indicates better wetting than a high angle and tends to be favoured by a low surface tension of the aqueous composition.

A measure of wetting appropriate to many textile processing operations is the amount of aqueous composition, expressed as a percentage of the weight of textile material, retained by the textile material after passage through a bath containing the aqueous composition and then between padding rollers.

As examples of cationic surface active agents there are mentioned quaternary salts such as alkyltrimethylammonium halides, alkylbenzyldimethylammonium halides, alkylpyridinium halides, alkylquinolinium halides, alkylimidazolinium halides and alkylmorpholinium halides, and preferably alkyltrimethylammonium halides and alkylpyridinium halides containing from eight to eighteen carbon atoms in the alkyl group. The agent may be a mixture of agents having a range of alkyl chain lengths.

As examples of anionic surface active agents there are mentioned alkylsulphates, e.g. sodium dodecylsulphate, optionally substituted aromatic sulphonates, e.g. sodium dodecylbenzenesulphonate, sodium naphthalenesulphonate, sodium oleyl-p-anisidinesulphonate, sodium dibenzylsulphanilate, the sodium salt of the condensation product of isopropanol with naphthalene-2-sulphonic acid, the sodium salts of condensates of aldehydes e.g. formaldehyde with aromatic sulphonic acids e.g. naphthalene-2-sulphonic acid, lignin sulphonates and sulphated natural oils, e.g. sulphated castor oil, sulphated sperm oil or sulphated methyloleate. The preferred anionic agents are salts of alkylbenzene sulphonic acids and of formaldehyde/naphthalene sulphonic acid condensates.

Mixtures of cationic or mixtures of anionic surface active agents may be used. The choice of cationic or anionic surface active agents may depend upon the other components of the aqueous composition. If, for example, the aqueous composition contains an affect material having a large organic anion it is desirable to use an anionic surface active agent to avoid precipitation caused by combination of the anion of the effect material with a surface-active cation and vice versa.

The alcohol, from which the ethylene oxide condensate is derived will preferably contain an alkyl group which is straight chain or only slightly branched, by which is meant not containing more than one tertiary carbon atom. As such alcohols there are mentioned for example octanol, decanol, dodecanol and alcohols obtained by carbonylation of olefins from petroleum fractions. As examples of the last there are mentioned $C_{7-9}$ alcohols containing about 45% of $C_7$, 40% of $C_8$ nd 15% of $C_9$ alcohols, and $C_{9-11}$ alcohols containing about 20% of $C_9$, 45% of $C_{10}$ and 35% of $C_{11}$ alcohols.

Mixtures of ethylene oxide condensates may be used. The preferred condensates contain from two to three molar proportions of ethylene oxide.

The ratio of the total amount of cationic or anionic surface active agents to the total amount of ethylene oxide condensates may be varied between very wide limits but will usually be within the range from 1:3 to 20:1.

The amounts of surface active agents and ethylene oxide condensates together may be varied within wide limits, the preferred amounts usually depending upon the amount and type of effect chemical and the surface to which it is to be applied.

Aqueous compositions suitable for applications to surfaces will normally contain only small amounts of effect materials, for example from 0.01 to 5.0% although amounts outside this range may be used in some cases, and amounts of surface active agent and ethylene oxide condensate together of 0.001% may confer adequate wetting properties. The preferred amounts in such compositions are from 0.01 to 5.0% but more can be used if desired although not usually giving a commensurate benefit.

It is however often convenient to prepare aqueous compositions which are more concentrated and which may contain up to more than 20% of surface active agent and ethylene oxide condensate together and amounts of effect material up to more than 20%, these concentrates being preferably diluted with an appropriate amount of water before use. These concentrates are not liable to phase separation and provide a convenient form in which the effect chemical may be stored, handled or transported and readily converted into a solution or dispersion suitable for application purposes.

The above aqueous compositions suitable for use, the concentrates, and aqueous compositions of intermediate concentration are all features of the invention.

If desired the aqueous compositions, especially the concentrates, may be converted to powders by drying, by any conventional method particularly spray drying. Such powders, which are very readily stored, handled and transported, are a further feature of the invention.

The aqueous compositions may contain other additives, such as corrosion inhibitors, if desired.

The aqueous compositions of the invention may be prepared by any conventional procedure suitable for the particular composition, for example by mixing the ingredients in any desired order at a convenient temperature, usually ambient temperature. If desired higher temperatures may be used in order to aid the mixing process. Since the surface-active agent and ethylene oxide condensate will frequently assist solution or dispersion of the effect material it is often desirable to mix the surface active agent and ethylene oxide condensate, preferably in that order, with the water before adding in the effect material. Mixing with only a small amount of the water to give a concentrated aqueous composition which is then diluted as desired is often the most convenient procedure.

The aqueous compositions of the invention have excellent wetting properties for surfaces which are normally difficult to wet, such as certain types of foliage, e.g. couchgrass or barley, certain textile materials having a hydrophobic surface such as synthetic materials, e.g. polyamides and polyesters or unscoured wool or cotton, textiles whose wettability is further limited by their construction, e.g. crimped polyester, knitted fabrics, and long piled carpet, oiled or greasy metals, plastics, soiled glass or ceramics and resin-coated ceramics. In addition the aqueous compositions may have increased fluidity compared with similar aqueous compositions which do not contain both surface active agent and ethylene oxide condensate.

According to the invention there is also provided a process for the application of effect materials to substrates which comprises treating the surface of the substrate with an aqueous composition of the invention.

The conditions of application will be determined in particular by the nature of the substrate and the effect material, and will in general be those used for application of the effect material concerned to that substrate from known types of aqueous medium. For example herbicides, insecticides and other agrochemicals will normally be sprayed on to, for example, foliage at ambient temperatures while dyestuffs may be applied by immersing the textile in the hot aqueous composition containing the dyestuff or by padding the textile with the aqueous composition, drying and baking.

In some cases it will be convenient to prepare the aqueous composition in situ, for example by mixing the water, surface active agent and ethylene oxide condensate, bringing the aqueous mixture so obtained into contact with the surface of the substrate, and then adding the effect material and continuing the treatment until the desired effect is obtained.

If desired the two stages in this last procedure may be separated, for example by treating the surface of the substrate with the mixture of water, surface active agent and ethylene oxide condensate, removing the substrate from this mixture, and then bringing the substrate into contact with an aqueous solution or dispersion containing the effect material and optionally surface active agent and ethylene oxide condensate. If desired the substrate may be dried in between the two treatments. This procedure is especially valuable in order to obtain homogenous dyeings of textiles which may have been poorly prepared, for example inefficiently scoured.

The invention is illustrated but not limited by the following Examples in which all parts and percentages are by weight unless otherwise stated.

EXAMPLE 1

A number of glass microscope slides are coated with paraffin wax (as an example of a surface which is difficult to wet) by dipping into a 10% solution of the wax in petroleum ether and allowing to dry.

Aqueous compositions containing surface-active agents and ethylene oxide condensates are prepared and the surface tension of each solution determined by the ring detachment method (du Nouy Tensiometer). Drops of these solutions are placed on the wax coated glass slides and their images projected on a screen enabling the contact angles to be measured.

The following table gives the surface tension and contact angle on paraffin wax for a number of aqueous compositions. Concentration is the percentage of surface active agent and ethylene oxide condensate together in the composition. When both an anionic or cationic surface active agent and an ethylene oxide condensate are present, the concentration of the two are equal. The figures illustrate the beneficial effect of the surface active agent and ethylene oxide condensate in conjunction. A similar beneficial effect is obtained in the aqueous compositions of the invention in which an effect material such as a polymeric biguanide biocide (where a cationic solubilising agent is used) or a reactive dyestuff e.g. Colour Index Reactive Yellow 3 (where an anionic solubilising agent is used) was also present.

EXAMPLE 3

Texturised polyester cloth is pad dyed using a Benz laboratory continuous dyeing machine. The dyebath liquor contains 4 parts of Colour Index Disperse Red 11, 10 parts of urea and 1 part of a 1:1 mixture of sodium dodecyl benzene sulphonate and a $C_9$–$C_{11}$ alcohol/2.5 moles ethylene oxide condensate per 100 parts of dyebath liquor. The padded cloth is dried for 90 seconds at 110°C and then baked for 60 seconds at 170°C. The dyed cloth shows significantly less two-sidedness compared with cloth dyed in the absence of the mixture of anionic surface active agent and ethylene oxide condensate and a more even penetration of dye-

| SURFACE ACTIVE AGENT | CONCENTRATION % | CONTACT ANGLE (DEGREES) | SURFACE TENSION (dyne.cm$^{-1}$) |
|---|---|---|---|
| 1. None (Pure Water) | — | >90 | 72.8 |
| 2. Tetradecyl trimethyl ammonium bromide ($C_{14}$TMAB) | 0.1 | 54 | 38.4 |
| 3. $C_{14}$TMAB/Dodecanol + 2 moles ethylene oxide | 0.1 | 20 | 23.8 |
| 4. $C_{14}$TMAB/Dodecanol + 3 moles ethylene oxide | 0.1 | 25 | 25.1 |
| 5. Hexadecyl pyridinium bromide ($C_{16}$PB) | 0.1 | 53 | 38.3 |
| 6. $C_{16}$P.B./Dodecanol + 4 moles ethylene oxide | 0.1 | 38 | 26.9 |
| 7. Hexadecyl trimethyl ammonium bromide ($C_{16}$TMAB) | 0.05 | 58 | 37.6 |
| 8. $C_{16}$TMAB/$C_{13}$–$C_{15}$ alcohol + 2 moles ethylene oxide | 0.05 | 29 | 26.7 |
| 9. $C_{16}$TMAB/$C_{13}$–$C_{15}$ alcohol + 3 moles ethylene oxide | 0.05 | 31 | 27.1 |
| 10. $C_{16}$TMAB/$C_{13}$–$C_{15}$ alcohol + 4 moles ethylene oxide | 0.05 | 34 | 27.0 |
| 11. $C_{14}$TMAB/$C_{13}$–$C_{15}$ alcohol + 4 moles ethylene oxide | 0.05 | 25 | 27.0 |
| 12. $C_{14}$TMAB/$C_9$–$C_{11}$ alcohol + 2 moles ethylene oxide | 0.05 | 20 | 29.1 |
| 13. $C_{14}$TMAB/$C_9$–$C_{11}$ alcohol + 3 moles ethylene oxide | 0.05 | 20 | 29.5 |
| 14. Sodium dodecyl benzene sulphonate (SDBS) | 0.1 | 42 | 31.4 |
| 15. SDBS/Dodecanol + 3 moles ethylene oxide | 0.1 | 28 | 29.4 |
| 16. Sodium dodecyl sulphate (SDS) | 0.1 | 66 | 34.3 |
| 17. SDS/Dodecanol + 3 moles ethylene oxide | 0.1 | 23 | 28.3 |
| 18. Sodium ligno sulphonate (SLS) | 0.1 | >80 | 67.1 |
| 19. SLS/Dodecanol + 3 moles ethylene oxide | 0.1 | 28 | 29.1 |
| 20. Sodium isopropyl naphthalene sulphonate (SIPNS) | 0.1 | 78 | 41.6 |
| 21. SIPNS/Dodecanol + 3 moles ethylene oxide | 0.1 | 30 | 30.0 |

EXAMPLE 2

Aqueous solutions containing sodium isopropyl naphthalene sulphonate and solutions containing at the same total concentrations a mixture of sodium isopropyl naphthalene sulphonate and a $C_9$–$C_{11}$ alcohol + 2.5 moles ethylene oxide condensate are prepared. Pieces of heavy cotton duck cloth (15 oz.) are padded by passage through the solutions followed by nipping in a mangle at a pressure of 25 kg/cm. The percentage pick up of moisture, measured by weighing the cloth before and after padding, in each case is given in the Table 2.

| Total Concentration of Agents % | Sodium isopropyl naphthalene sulphonate | 1:1 Sodium isopropyl naphthalene sulphonate & $C_9$–$C_{11}$ alcohol + 2.5 moles ethylene oxide |
|---|---|---|
| 0.05 | 7.60 | 11.50 |
| 0.10 | 9.14 | 13.80 |
| 0.20 | 11.25 | 17.40 |
| 0.50 | 18.35 | 25.00 |

At each concentration there is an increase in the moisture pick up for those solutions containing both anionic surface active agent and the ethylene oxide condensate. Similar results are obtained in the presence of an effect material such as dyestuff C.I. Reactive Yellow 3.

stuff throughout the cloth, indicating better wetting of the cloth during the padding operation and a maintenance of the wetting during the drying of the cloth.

EXAMPLE 4

Unglazed dinner plates are printed with a resin based decorative transfer and allowed to dry. A glaze slurry is applied containing 0.2% of a mixture of 25% of the sodium salt of sulphonated methyl oleate, 10% of dodecyl alcohol/3 moles ethylene oxide condensate and 65% of water. Pottery treated in this way gives a smooth glazed finish whereas pottery to which glaze is applied without the addition of the anionic surface active agent and ethylene oxide condensate gives an uneven finish due to incomplete wetting of the hydrophobic transfer surface.

EXAMPLE 5

An aqueous dyestuff dispersion is prepared by milling 32.4 parts of Colour Index Disperse Red 82, 57.9 parts of a 50% aqueous solution of a 1:1 mixture of the sodium salt of a condensation product of formaldehyde and naphthalene-2-sulphonic acid and a $C_9$–$C_{11}$ alcohol/2.5 moles ethylene oxide condensate, 16.2 parts of glycerol, 1.6 parts of a 20% aqueous solution of a phenolic bactericide and 11.9 parts of water. The resulting dyestuff dispersion is passed through a 300 mesh sieve and tested by diluting 15 parts of the dispersion with 800 parts of distilled water, and passing through a piece of 65/35 polyester/cotton cloth stretched over a 7 inch embroidery frame, the cloth being then washed with 200 parts of distilled water, dried at 110°C and baked at 220°C for 1½ minutes.

Visual examination of the cloth shows a marked reduction in the number of specks caused by the presence of oversized particles, compared with a similar test cloth prepared from a dispersion which contained only anionic surface active agent in comparable amount.

EXAMPLE 6

2-Ethylamino-5-n-butyl-4-hydroxy-6-methyl pyrimidine is prepared for application as a seed dressing by grinding a slurry of 50 parts of the pyrimidine, 2 parts of a 1:1 mixture of the sodium salt of a condensate of formaldehyde with naphthalene-2-sulphonic acid and a $C_9$–$C_{11}$ alcohol/2.5 moles ethylene oxide condensate and water to a total of 100 parts. The slurry is a fluid paste and grinds easily whereas a slurry prepared using 2 parts of the anionic agent alone is a thick paste which requires a treatment such as high speed mixing in order to wet out the fungicide and fluidise before grinding is carried out. This slurry may be used as a seed dressing.

The ground slurry is diluted with water to a strength of 0.015% of pyrimidine derivative and is applied to barley as a fungicidal spray, showing excellent wetting of the foliage whereas a similar fungicidal spray prepared using the anionic surface active agent alone has poor foliage wetting properties on barley.

EXAMPLE 7

Aqueous solutions containing the sodium salt of sulphated methyl oleate and solutions containing at the some total concentrations a mixture of sodium dodecyl benzene sulphonate and a $C_7$–$C_9$ alcohol/2.5 moles ethylene oxide condensate are prepared. Pieces of heavy cotton duck cloth (15 oz.) are padded by passage through the solutions, followed by nipping in a mangle at a pressure of 25 kg./cm. The percentage pick up of moisture, measured by weighing the cloth before and after padding in each case is given in the Table 3.

| Total Concentration of Agents % | Sulphonated Methyloleate Sodium Salt | 1:1 Sodium dodecyl benzene sulphonater $C_7$–$C_9$ alcohol + 2.5 moles ethylene oxide |
|---|---|---|
| 0.05 | 9.31 | 11.28 |
| 0.10 | 10.37 | 14.28 |
| 0.20 | 12.11 | 18.41 |
| 0.50 | 15.87 | 28.95 |

At each concentration there is an increase in the moisture pick up for those solutions containing both anionic surface active agent and the ethylene oxide condensate. Similar results are obtained when the aqueous solution contain an affect material such as C.I. Reactive Yellow 3.

EXAMPLE 8

A dyebath is prepared, for use in the dyeing of polyamide carpet composed of:

| | |
|---|---|
| Colour Index No. Acid Red 57 | 1 part |
| Sodium dihydrogen phosphate | 5 part |
| Sodium dodecyl benzene sulphonate/$C_7$–$C_9$ alcohol/2.5 moles ethylene oxide condensate mixture in the ratio 1:2 as 50% active agent | 5 part |
| Water | to 1000 parts |

Nylon 66 loop poled tufted carpet is slop-pad dyed by dipping the carpet in a tray containing the dye-liquor and hanging the carpet up to allow drainage of the excess liquors. The carpet containing dye liquor is held in an atmosphere of steam for 10 minutes to fix the dyestuff and the excess dyestuff then removed by washing with cold water. Carpet dyed in this manner with the agent present showed no frostiness due to inhomogeneous dyeing. Whereas a sample of carpet dyed in the absence of the agent showed considerable frostiness, demonstrated by white tips on the carpet pile due to incomplete wetting by the dyestuff liquors.

EXAMPLE 9

A dyestuff paste is prepared for the printing of polyamide carpet having the composition:

| | |
|---|---|
| Colour Index No. Acid Black 48 | 10 part |
| Sodium dodecyl benzene sulphonate/$C_7$–$C_9$ alcohol/2.5 moles ethylene oxide condensate mixture in the ratio 1:2, as 50% active agent | 5 part |
| Citric Acid | 7.5 part |
| Modified locust bean gum thickener, as 4% solution | 300 part |
| Water | 1000 part |

Nylon 66 loop piled tufted carpet is printed using a dyestuff paste impregnated foam pad which is pressed on to the carpet under standard conditions. The printed carpet is held in an atmosphere of steam for 10 minutes, excess dyestuff rinsed off and the carpet dried. Carpet printed in the presence of the wetting agent showed no frostiness due to inhomogeneous wetting of the pile whereas carpet printed without the wetting agent showed considerable frostiness.

EXAMPLE 10

A bactericidal spray formulation for the treatment of animal hide is prepared having the composition:

| | |
|---|---|
| A polymeric biguanide biocide as hydrochloric salt | 20 parts |
| cetyl trimethyl ammonium bromide | 4.125 parts |
| $C_9$–$C_{11}$ alcohol/2.5 moles ethylene oxide condensate | 0.125 parts |
| Water to 100 parts | |

The formulation is sprayed on to flayed animal hides immediately after slaughter. The hides were kept for seven days at 25°–27°C and examined for degradation. Hides sprayed with biocide in the presence of the wetting agent showed less degradation than hides sprayed with biocide alone, due to greater penetration of the hairy hide surface by the spray containing the wetting agent.

In the above formulation an unusually high proportion of cetyl trimethylammonium bromide is used in order to take advantage of the antibacterial effect of this compound.

EXAMPLE 11

A spinning lubricant system for use in the spinning of polyester yarn is prepared having the composition:

| | |
|---|---|
| stearic acid/9 moles ethylene oxide condensate (spin lubricant) | 4 parts |
| Water to 100 parts | |

Similar mixtures are prepared containing 0.8–2 parts of a 50% active agent mixture of sodium dodecyl benzene sulphonate and a $C_9$–$C_{11}$ alcohol/2.5 moles ethylene oxide condensate. Drops of the formulations are placed on "Melinex" polyester film (Melinex is a registered trade mark) and their contact angles measured, the results are given in Table 4.

| Part of Wetting | Contact Angle (degrees) |
|---|---|
| 0 (Control) | 33 |
| 0.8 | 26 |
| 1.2 | 22 |
| 2.0 | 14 |

In each case, addition of the wetting agent mixture improved the wetting of the polyester film by the lubricant system. An additional improvement was a marked increase in the fluidity of the formulation when the wetting agent mixture was present.

EXAMPLE 12

Solutions of a polymeric bi-guanide biocide were prepared at 0.2% active agent strength containing 0, 0.04, 0.10 and 0.2 parts of a 50% active agent mixture of cetyl trimethyl ammonium bromide with a $C_9$–$C_{11}$ alcohol/2.5 moles ethylene oxide condensate in the ratio 1:1. The contact angles of drops of the solutions on paraffin wax coated microscope slides were measured, the results are given in Table 5.

| Parts of Wetting Agent | Contact Angle (degrees) |
|---|---|
| 0 (Control) | >120° |
| 0.04 | 32 |
| 0.10 | 23 |
| 0.20 | 21 |

In each case the addition of the wetting agent mixture has markedly improved the ability of the biocide solution to wet the paraffin wax surface.

EXAMPLE 13

4000 Parts of Colour Index Acid Red 266 paste (66.3% total solids equivalent to 2652 parts dry colour) are mixed with 3310 parts of a 50% aqueous solution of a 1:1 mixture of the sodium salt of dodecyl benzene sulphonate and a condensate of $C_9$–$C_{11}$ alcohol with 2.5 moles of ethylene oxide. The suspension is dried in an oven at 70°C and the resultant product ground and standarised with 2652 parts dextrine in a mill. The solid product contains 40% of dyestuff, 10% of sodium dodecyl benzene sulphonate, 10% of ethylene oxide condensate, 40% of dextrine.

7.5 Parts of the product are suspended in 250 parts of water. The suspension is heated to 100°C with stirring to dissolve the powder. The solution when cooled to room temperature is fluid and non-gelatinous and very suitable for use in dyeing polyamide textile materials. It is particularly valuable for use in cold dyeing applications since solutions of Colour Index Red 266 but not containing the anionic agent and ethylene oxide condensate gel when cold even at concentrations as low as 0.5%.

Similar powders and solutions suitable for cold dyeing are obtained by the above powder if the sodium dodecylbenzenesulphonate is replaced by the sodium salt of a condensation product of formaldehyde and naphthalenesulphonic acid, or by a procedure in which the dextrine is added before drying and the standardised solution then spray dried.

We claim:

1. Aqueous surface active agent compositions having improved wetting properties for use in applying dyestuffs to solid surfaces which contain,
   one or more cationic surface active agents selected from the group consisting of alkyltrimethylammonium halides, alkylbenzyldimethylammonium halides, alkylpyridinium halides, alkylquinolinium halides, alkylinidazolinium halides and alkylmorpholinium halides, or
   one or more anionic surface active agents selected from the group consisting of the sodium salts of alkyl sulphates, aromatic sulphonates, condensates of aldehydes and aromatic sulphonic acids, lignin sulphonates and of sulphated natural oils, and
   one or more condensates of from 2 to 3 molar proportions of ethylene oxide with an aliphatic alcohol containing from seven to fifteen carbon atoms, the ratio of cationic/anionic agent to ethylene oxide condensate in the range of 1:3 to 20:1, the total amount of cationic/anionic agent together with ethylene oxide condensate is from 0.01 to 5% of the aqueous composition and from 0.01 to 5.0% of dyestuff.

2. Aqueous compositions as claimed in claim 1 wherein the aliphatic alcohol contains an alkyl group containing not more than one tertiary carbon atom.

3. Powder compositions comprising a dyestuff, one or more cationic or one or more anionic surface active agents and one or more condensates of from 2 to 3 molar proportions of ethylene oxide with an aliphatic alochol containing from seven to fifteen carbon atoms, prepared by spray drying an aqueous composition as claimed in claim 1.

4. A process for the preparation of surface active compositions as claimed in claim 1 which comprises mixing in any order water, one or more cationic or one or more anionic surface active agents, one or more condensates of from one to four molar proportions of ethylene oxide with an aliphatic alcohol containing from seven to fifteen carbon atoms, and at least one dyestuff.

5. A process as claimed in claim 4 wherein the cationic or anionic surface active agents, ethylene oxide condensates and dyestuff are mixed in that order with water.

6. A process for the treatment of a solid substrate with a dyestuff which comprises applying to the substrate an aqueous composition as claimed in claim 1.

7. A process comprising the steps of mixing in any order water, one or more cationic or one or more anionic surface active agents and one or more condensates of from one to four molar proportions of ethylene oxide with an aliphatic alcohol containing from seven to fifteen carbon atoms to give an aqueous composition as claimed in claim 1, applying the aqueous composition to a substrate by immersion, removing the substrate from the aqueous composition, and applying to the substrate an aqueous solution or suspension of a dyestuff.

8. Aqueous compositions as claimed in claim 1 wherein said anionic surface active agent is selected from the group consisting of sodium dodecylsulphate, sodium dodecylbenzenesulphonate, sodium naphthalenesulphonate, sodium oleyl-p-anisidinesulphonate, sodium dibenzylsulphanilate, the sodium salt of the condensation product of isopropanol with napthalene-2-sulphonic acid, napthalene-2-sulphonic acid, sulphated castor oil, sulphated sperm oil and sulphated methyloleate.

9. Aqueous compositions as claimed in claim 1 wherein said anionic surface active agent is the salt of an alkylbenzene sulphonic acid or a formaldehyde/-naphthalene sulphonic acid condensate.

10. Aqueous compositions as claimed in claim 1 wherein said cationic surface active agent is an alkyltrimethylammonium halide or an alkylpyridinium halide each having from 8 to 18 carbon atoms in the alkyl group.

* * * * *